United States Patent
Koehler et al.

(10) Patent No.: US 12,272,036 B2
(45) Date of Patent: Apr. 8, 2025

(54) SYSTEM AND METHOD FOR CORRECTING MOTION ARTIFACTS BY COMBINING IMAGES IN PHASE-CONTRAST AND DARK-FIELD IMAGING APPLICATIONS

(71) Applicant: KONINKLIJKE PHILIPS N.V., Eindhoven (NL)

(72) Inventors: Thomas Koehler, Norderstedt (DE); Andriy Yaroshenko, Garching (DE); Hanns-Ingo Maack, Norderstedt (DE); Thomas Pralow, Buchholz (DE); Bernd Lundt, Flintbek (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 344 days.

(21) Appl. No.: 17/778,946

(22) PCT Filed: Nov. 20, 2020

(86) PCT No.: PCT/EP2020/082799
§ 371 (c)(1),
(2) Date: May 23, 2022

(87) PCT Pub. No.: WO2021/105009
PCT Pub. Date: Jun. 3, 2021

(65) Prior Publication Data
US 2022/0414844 A1    Dec. 29, 2022

(30) Foreign Application Priority Data
Nov. 28, 2019    (EP) .................................... 19212117

(51) Int. Cl.
*G06T 5/80*    (2024.01)
*G06T 5/50*    (2006.01)
*G06T 7/20*    (2017.01)

(52) U.S. Cl.
CPC .................. *G06T 5/80* (2024.01); *G06T 5/50* (2013.01); *G06T 7/20* (2013.01); *G06T 2207/10116* (2013.01); *G06T 2207/20212* (2013.01)

(58) Field of Classification Search
None
See application file for complete search history.

(56) References Cited

U.S. PATENT DOCUMENTS

| 2014/0185746 | A1* | 7/2014  | Baturin | G21K 1/06 378/36 |
| 2017/0209108 | A1* | 7/2017  | Grass   | A61B 6/4291 |
| 2022/0414844 | A1* | 12/2022 | Koehler | G06T 5/50 |

FOREIGN PATENT DOCUMENTS

| WO | WO2017176976 A1 | 10/2017 |
| WO | WO2018046600 A2 | 3/2018 |

(Continued)

OTHER PUBLICATIONS

PCT International Search Report, International application No. PCT/EP2018/082799, Jan. 12, 2021.

(Continued)

*Primary Examiner* — Tahmina N Ansari
(74) *Attorney, Agent, or Firm* — Larry Liberchuk (57) ABSTRACT

A system (IPS) and related method for image processing, in particular dark-field or phase contrast imaging to reduce motion artifacts. The system comprises an input interface (IN) for receiving a series of projection images (π) acquired by an X-ray imaging apparatus (XI) of an object (OB) for a given projection direction, the imaging apparatus (XI) configured for phase-contrast and/or dark-field imaging A phase-contrast and/or dark-field image generator (IGEN) applies an image generation algorithm to compute a first image based on the series the projection images (π). A motion artifact detector (MD) detects a motion artifact in the (Continued)

first image. A combiner (Σ) combines, if a motion artifact is so detected, a part of the first image with a part of at least one auxiliary image to obtain a combined image. The auxiliary image was previously computed by a gated application of the image generation algorithm in respect of a subset of the series of the projection images (π). The combined image may be output at an output interface (OUT) as a motion artifact reduced image.

11 Claims, 4 Drawing Sheets

(56) References Cited

FOREIGN PATENT DOCUMENTS

| WO | WO2018046600 A3 | 3/2018 |
| WO | WO2018115215 A1 | 6/2018 |

OTHER PUBLICATIONS

Velroyen A. et al., "Dissertation X-Ray Phase-Contrast and Dark-Field Imaging of Small Animals: Contrast Enhancement and In Vivo Imaging", Mar. 6, 2015 (Mar. 6, 2015), pp. 1-172, XP055684508.

Gromann L.B. et al., "In-Vivo X-Ray Dark-Field Chest Radiography of a Pig", Scientific Reports, vol. 7, No. 1, Jul. 6, 2017 (Jul. 6, 2017), XP055405084.

Yaroshenko A. et al., "Pulmonary Emphysema Diagnosis with a Preclinical Small-Animal X-Ray Dark-Field Scatter-Contrast Scanner", Radiology, vol. 269, No. 2, pp. 427-433, Nov. 2013.

Pfeiffer F. et al., "Hard-X-Ray Dark-Field Imaging Using a Grating Interferometer", Nature Materials, vol. 7, pp. 134-137, 2008.

Wen H, et al., "Fourier X-Ray Scattering Radiography Yields Bone Structural Information", Radiology, vol. 251, No. 3, pp. 910-918, Jun. 2009.

Seifert M. et al., Single-Shot Talbot-Lau X-Ray Dark-Field Imaging of a Porcine Lung Applying the Moire Imaging Approach, Physics in Medicine & Biology, Institute of Physics and Engineering in Medicine, vol. 63, pp. 1-13, 2018.

Weitkamp T. et al., "X-Ray Phase Imaging with a Grating Interferometer", Optics Express, vol. 13, No. 16, pp. 6296-6304, Aug. 2005.

* cited by examiner

SYSTEM AND METHOD FOR CORRECTING MOTION ARTIFACTS BY COMBINING IMAGES IN PHASE-CONTRAST AND DARK-FIELD IMAGING APPLICATIONS

FIELD OF THE INVENTION

The invention relates to a system of image processing, a method of image processing, a computer readable medium, and a computer program element.

BACKGROUND OF THE INVENTION

Dark-field imaging has attracted much interest especially in the medical field. Dark-field ("DAX")-imaging is a type of X-ray imaging. Contrast in dark-field imaging relates to the amount of small angle scatter experienced by the X-radiation.

Experimental dark-field imaging with mice have been reported by A. Yaroshenko et al in "*Pulmonary Emphysema Diagnosis with a Preclinical Small-Animal X-ray Dark-Field Scatter-Contrast Scanner*", Radiology, vol. 269, No 2, November 2013.

Phase-contrast ("$\Phi$"-)images have also been found to add additional useful insights, in particular when imaging soft-tissue.

It has been overserved that at times DAX- or phase-contrast $\Phi$-images are corrupted by motion artifacts.

SUMMARY OF THE INVENTION

There may therefore be a need for alternative systems or methods to improve dark-field or phase-contrast imaging.

The object of the present invention is solved by the subject matter of the independent claims where further embodiments are incorporated in the dependent claims. It should be noted that the following described aspect of the invention equally applies to the image processing method, the image processing system, to the computer program element and to the computer readable medium.

According to a first aspect of the invention there is provided a system for image processing, comprising:

an input interface for receiving a series of projection images acquired by an X-ray imaging apparatus of an object for a given projection direction, the imaging apparatus configured for phase-contrast and/or dark-field imaging;

a phase-contrast and/or dark-field image generator configured to apply an image generation algorithm to compute a first image based on the series the projection images ($\pi$);

a motion artifact detector configured to detect a motion artifact in the first image;

a combiner configured to combine, if a motion artifact is so detected, at least a part of the first image with at least a part of at least one auxiliary image to obtain a combined image, the auxiliary image previously computed by a gated application of the image generation algorithm in respect of a subset of the series of the projection images ($\pi$); and an output interface to output the combined image.

The proposed system allows addressing one reason why dark-field or phase-contrast imagery has been observed to suffer from motion artifacts. This reason is as follows. Some image generation algorithms, such as phase retrieval algorithms, use a signal model. The signal model assumes a stationary object. If the object does move, the stationary assumptions are violated and this yields image artifacts. The proposed system accounts for this motion by implementing adaptive gating in the image generation algorithm. Specifically, some image generation algorithms include fitting the signal model to the measured projection imagery. The fitting operation is formulated as optimization of an objective function, such as a cost function. Specifically, the proposed system can be considered a two-step approach. Since motion creates data which is inconsistent with the signal modelling that underlies some phase retrieval algorithms, the objective function after optimization has been found to typically return values that are much larger than what is statistically expected. In embodiments, this observed fact is harnessed in the proposed system to reduce the motion artifacts. The combined image includes information from both, the first image and certain ones of the auxiliary images (the gated images) to reduce the motion artifacts.

The motion detection by motion detector is based on information in the first image and/or on analysis of additional information. This additional information may include an analysis of whether a "mis-fit" as measured by the objective function is within a range that can be expected statistically. In embodiments, one may re-apply the model to calculate the mis-fit from the first image and the projection images.

According to one embodiment, the system comprises a selector configured to select, in a selection operation, the auxiliary image from a pool of such auxiliary images computed based on different such subsets.

According to one embodiment the image generation algorithm is based on an objective function. The image generation algorithm adjusts fitting variable(s) of a signal model to fit the measured data (projection images). The algorithm improves the objective function when adjusting the fitting variables. Some or the fitting variables represent the DAX or $\Phi$-image to be obtained.

According to one embodiment wherein the selection operation is based on a score.

According to one embodiment the score includes a value returned by the objective function.

According to one embodiment, the motion detector is configured to detect the motion artifact based on a value of the objective function for the said first image.

According to one embodiment, the system comprises a sanity checker, configured to compute, based on a second subset, a series of transmission images and pairwise differences with the combined image, and to retain, at an image location in the combined image, image information from the first image, if the difference values are found to propagate through the series of transmission images. In this embodiment, the sanity checker operates downstream the combiner.

However, there are also alternative embodiments envisaged, where the sanity checker operates upstream the combiner. In one such upstream embodiment, the series of projection images as received at the input interface are provided by the sanity checker as a sub-set from an original set of projection images, the sanity checker previously computing, from the said original set of projection images, transmission images, and the sanity checker configured to exclude, based on the transmission images, one or more images from the original set of projection images, wherein the excluded one or more projection mages represent linear motion at at least one image location.

The sanity checker is advantageous in helping to avoid artifacts that may be caused in the presence of transitory, non-periodic motion such as linear motion. If the motion is periodic, the sanity checker may not be required.

According to another aspect there is provided a method of image processing, comprising the steps of:

receiving a series of projection images acquired by an X-ray imaging apparatus of an object for a given projection direction, the imaging apparatus configured for phase-contrast and/or dark-field imaging;

applying an image generation algorithm to compute a first image based on the series the projection images;

detecting a motion artifact in the first image;

combining, if a motion artifact is so detected, at least a part of the first image with at least a part of at least one auxiliary image to obtain a combined image, the auxiliary image previously computed by a gated application of the image generation algorithm in respect of a subset of the series of the projection images; and outputting the combined image.

According to one embodiment, the method further comprises:

i) computing, based on a second subset, a series of transmission images and pairwise differences with the combined image, and to retain, at an image location in the combined image, image information from the first image, if the difference values are found to propagate through the series of transmission images; or ii) wherein the series of projection images as received are provided as a sub-set from an original set of projection images, obtained by:

computing, from the said original set of projection images, transmission images, and excluding, based on the transmission images, one or more images from the original set of projection images, wherein the excluded one or more projection mages represent linear motion at at least one image location.

According to another aspect there is provided an imaging arrangement, comprising:

a system of any one of previously mentioned embodiments;

the X-ray imaging apparatus; and a display device.

In one embodiment, the X-ray imaging apparatus is of slot-scanning type or of full-view type.

In one embodiment, the X-ray imaging apparatus includes an interferometer.

According to another aspect there is provided a computer program element, which, when being executed by at least one processing unit, is adapted to cause the processing unit to perform the method as any one of the above mentioned embodiments.

According to another aspect there is provided at least one computer readable medium having stored thereon the program element.

"Gated application" of the image generation algorithm in respect of the subset of projection images includes restricting the image generation algorithm to only projection images from the said sub-set. However, the said gated application of the image generation algorithm also includes application to projection image(s) outside the subset (so all projection images may be processed), but projection images in the subset are given more weight relative to projection images outside the subset.

"Image generation algorithm" include in particular phase retrieval algorithms or other image generation schemes that are configured to extract or isolate dark field imagery and/or phase contrast imagery from a series of projection images. The acquisition of the series of projection images may have been facilitated by inclusion of additional imaging hardware structures into the X-ray imaging apparatus, such as in grating-based imaging (eg, interferometry), coded apertures, or other at least partially radiation blocking structures with periodic or non-periodic sub-structures, or others. The image generation algorithm may include optimizing a fit of the measured data (the projection images) to a signal model. The optimization is to improve a cost function that measures the mis-fit between values as per the signal model and the measured data.

The imaged "object" is animate and includes a human or animal patient or a part thereof, or the object is inanimate such as an item or luggage in a security screening system or a sample object in non-destructive material testing.

"User" include a person (eg, a healthcare professional) who operates the imaging apparatus and/or system to image the object.

BRIEF DESCRIPTION OF THE DRAWINGS

Exemplary embodiments of the invention will now be described with reference to the following drawings, which are not to scale, wherein.

DETAILED DESCRIPTION OF EMBODIMENTS

Figure 1:
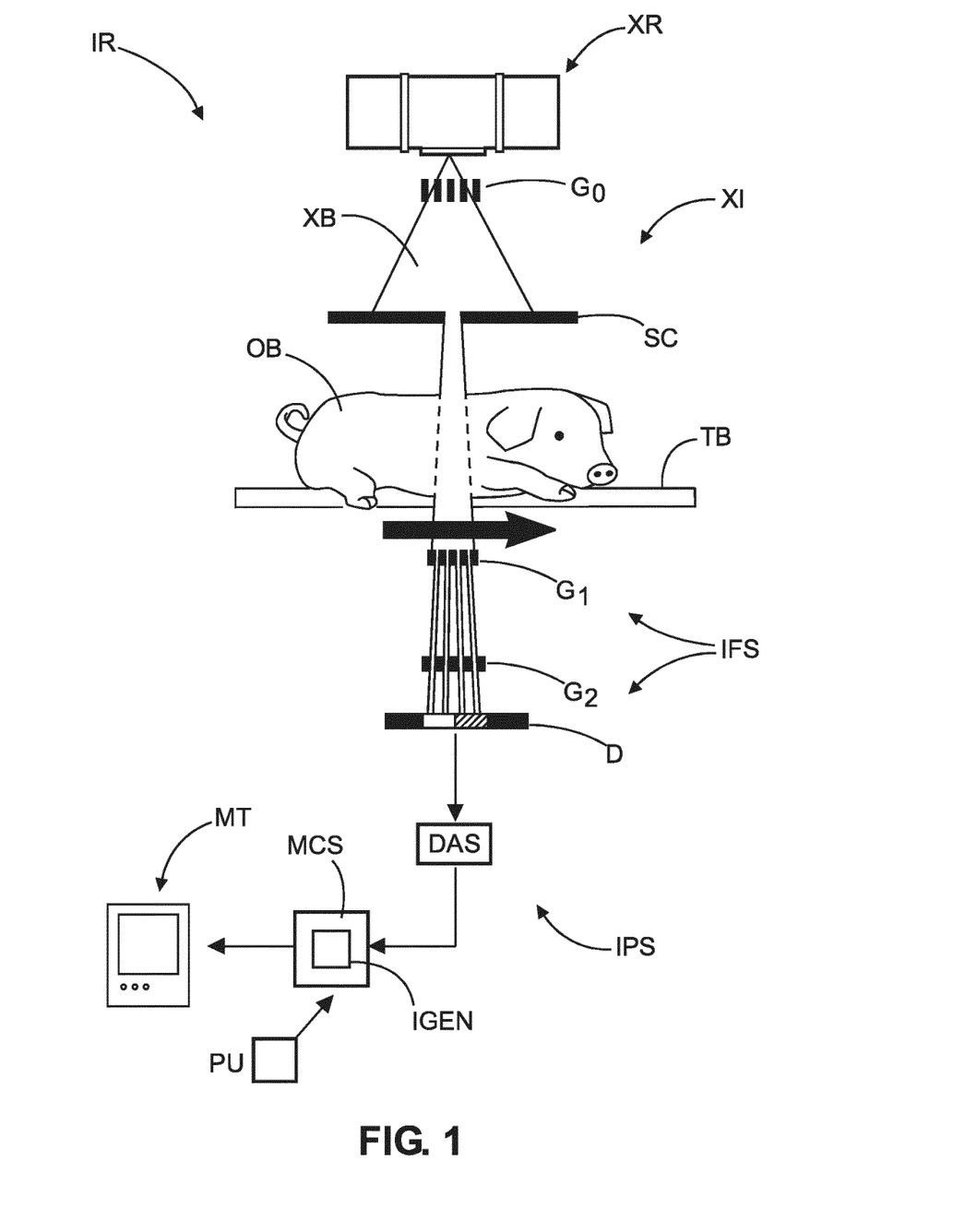
FIG. 1 is a schematic block diagram of an X-ray imaging apparatus configured for phase-contrast or dark-field imaging.

With reference to FIG. 1, there is shown a schematic block diagram of an image processing arrangement IA that includes a computerized image processing system IPS and an X-ray imaging apparatus XI ("imager"). The X-ray imaging apparatus is configured for dark-field X-ray ("DAX"-) imaging and/or phase-contrast ("Φ"-) imaging.

The image processing system IPS may be run one or more software modules or routines on one or more processing units PU such as one or more computers, servers, etc. The IPS may be arranged externally and remote of the imager XI or the IPS is integrated into or associated with the imager XI, for instance into one or more processing units PU of the imager XI, such a work station. The image processing system IPS may be implemented in a distributed architecture to serve a group of imagers over a suitably communication network. Some or all components of the IPS may be arranged in hardware such as a suitably programmed FPGA (field-programmable-gate-array) or as hardwired IC chip.

Broadly, the image processing system IPS includes an image generator IGEN that processes projection imagery it acquired by the imager XI into dark-field and/or phase-contrast imagery. The projection imagery it is sometimes referred to herein as "frames". The image processing system IPS includes a motion correction system MCS ("motion corrector") to reduce motion artifacts in the imagery that are due to, in particular, patient OB motion during acquisition of the projection imagery π. The motion corrected imagery as provided by the motion correction system MCS can then be displayed on a display unit MT or can be stored in a memory for later review, or can be otherwise further processed.

Although in FIG. 1 it is envisaged that the imaging apparatus XI supplies the projection imagery π directly, via wireless or a wired connection, to the image processing system IPS, this may not be so in all embodiments. For instance, the projection imagery it may be first stored in a memory such as in a picture archiving system (PACS) of a hospital information system (HIS) or otherwise, and the imagery to be processed is retrieved at a later stage (e.g. upon user request) by the IPS and is then processed.

In general, the imaging apparatus XI includes an X-ray source XR, an X-radiation sensitive detector D, and an imaging facilitator structure IFS, such as an interferometer, arranged in between the source XR and the detector D. The X-ray source XR generates an X-ray beam XB which is detectable by the detector D. The imaging facilitator structure IFS is a device, or a group of devices, that allows translating X-ray beam XB refraction and/or small angle scattering of the beam XB into intensity modulations at the detector D, thereby facilitating resolving said modulations into dark-field and/or phase-contrast image signals and, if desired, into an attenuation image signal.

In the following, main reference will be made to an interferometric imaging apparatus XI including the interferometer as the imaging facilitator structure IFS, although this is not to exclude embodiments that use other, in particular non-interferometric, imaging facilitator structures IFS. Such non-interferometric imaging facilitator structures IFS include for example coded aperture systems. In general, the dark-field or phase-contrast is obtainable by the imaging facilitator structure IFS imparting a periodic wave front modulation on the incoming imaging X-ray beam and a measurement, by the X-ray detector D, of a variation of the resulting wave-front caused be the object OB to be imaged.

Turning now in more detail to the imaging apparatus XI, this can be a configured for 2D imaging such as a radiography apparatus or for 3D imaging such as a CT scanner. Between the X-ray source XR and the detector D there is defined an imaging region where the object OB (e.g., the chest of the subject) to be imaged resides during imaging. In the imaging region there is arranged an interferometer as one embodiment of the imaging facilitator structure IFS. The interferometer includes a single, two or three (or more) grating structures. As said above, the interferometer is but one embodiment of the image facilitator structure IFS and we will make main reference to this embodiment in the following, with the understanding that the principles of the present disclosure are not confined to interferometry but can be readily extended to other grating-based or non-grating based structures as other embodiments of the image facilitator structure IFS as mentioned above.

With continued reference to the (non-limiting) interferometric embodiment of the image facilitator structure IFS, periodicity, aspect ratio, etc. of the gratings are such that they cause diffraction of the X-ray beam and/or just enough coherence is achieved so that the small-angle scattering can be detected or derived. Absorption and phase gratings may be used. In one embodiment the gratings are formed by photolithography or cutting in silicon wafers to define a periodic pattern of trenches. Interspaces between the trenches may be filled with lead or gold for the absorption gratings. Instead of such gratings, crystal structures may be used.

In yet more detail and in one embodiment, an absorbing grating structure G2 is arranged between the detector D and the object OB whilst the other grating G1, a phase grating, is arranged between the object OB and the X-ray detector D. In some embodiments there is also an additional grating G0 arranged at the X-ray source XR, in case the X-ray source is incapable of generating natively coherent radiation. If the X-ray source produces incoherent radiation (which is usually the case), the (absorption) grating G0 at the X-ray source (also referred to as the source grating) transforms the X-radiation coming out of the X-ray source into an, at least partly, coherent radiation beam XB. Inverse geometries where G1 is placed upstream the object OB, i.e. between XR and OB, are also envisaged.

The at least partly coherent radiation beam XB propagates through the imaging region and interacts with the interferometer IFS and the patient OB. After said interaction, the radiation is then detected in form of electrical signals at radiation sensitive pixel elements of the detector D. Data acquisition circuitry DAS digitalizes the electrical signals into projection (raw) image data $\pi$ which is then processed by the IPS in a manner explained in more detail below.

The imaging apparatus XI may be of the full field-of-view (FoV) type, where the detector is of the flat panel type. In full FoV imaging system, the size of the detector D and the size of the IFS corresponds to the desired FoV. Alternatively, the detector D and the imaging facilitator structure IFS may be smaller than the intended FoV such as in slot-scanning systems as shown in FIG. 1. In some of these systems, the detector comprises a discrete series of detector lines. The detector lines are mounted on a scan arm to be scanned across the intended FoV in different slot-positions.

Slot-scanning systems as shown in in FIG. 1 are more cost effective than full FoV system because they require smaller detectors and smaller gratings IFS. The gratings IFS are mounted on the scan arm above the detector and are equally scanned across the FoV. In alternative slot-scanning systems, although the detector D has the same size as the desired FoV, the gratings are smaller and a collimation SC is used to scan only parts of the FoV (in "slots") at any one time as per the collimation. In a full FoV system and slot scanning systems with a non-moving flat panel detector, there is a simple one-to-one relationship between pixel position and imaginary geometrical rays that pass through the imaging region to define the imaging geometry. The rays extend from a focal spot of the X-ray source XR and intersect the detector plane at the respective pixel positions. Each one of the geometrical rays corresponds to a respective, different, single one of the pixels. No such simple relationship exists in some slot-scanning system with smaller detector, where each geometrical ray is seen by many different pixels in different "slots" during the scanning. Signals from different pixels are then processed together by a suitable logic for any single geometrical ray.

The image generator IG outputs the dark-field signals and/or the phase-contrast signals as respective arrays of image values which form the dark-field image and the phase-contrast image, respectively. These image values or pixel values represent respectively the contrast for the dark-field signal and the phase-change experienced by the X-radiation while traveling through the object OB, for the respective geometrical ray.

Generally, when X-radiation interacts with material, it experiences both attenuation and refraction and hence phase change. The attenuation on the other hand can be broken down into attenuation that stems from photo-electric absorption and attenuation that comes from scatter. The scatter contribution in turn can be decomposed into Compton scattering and Rayleigh scattering. For present purposes of dark-field imaging it is the small angle scattering that is of interest, where "small angle" means that the scatter angle is so small that the scattered photon still reaches the same pixel as it would have reached without being scattered.

The dark-field contribution can be modelled as visibility $V = V_0 * e^{-\int E(z)dz}$, with $\varepsilon$ is the spatial distribution of the diffusion property of the patient OB and the integration is performed along the x-ray beam path, and $V_0$ being the reference visibility without object interaction (recorded in a calibration measurement). The dark-field signal as recorded in the dark-field image is then $D=V/V_0$.

Traditional radiography systems are usually incapable of resolving the detected signal into dark-field contribution. But by using the interferometer IS as shown in in FIG. 1, or by using other imaging facilitator structures IFSs, it is possible to translate these contributions into an intensity pattern of fringes which can be analyzed by the image generator IGEN to obtain the phase-contrast and/or DAX image.

Turning now in more detail to the image generator IGEN, this operates on a series of projection images obtained in a phase stepping operation. Based on this recorded series of projection images, the image generator IGEN computationally resolves the detected fringe pattern in the series projection data into three contributions or signals, namely the refraction contribution (also referred to as the phase-contrast signal), a dark-field signal component and a remaining attenuation component.

Because of these three contrast mechanisms acting together, the signal processing by the IGEN of the detected series of intensities proceeds in three signal channels (phase-contrast, dark-field, and attenuation).

In the above described types of imaging system, the capability for dark-field/phase-contrast imaging is achieved as follows: the projection data is acquired at the detector D during the phase stepping operation as a series for a given fixed projection direction. The phase of the fringes is typically stepped over 360°. The phase stepping operation is typically realized by inducing a motion between X-ray beam and of the image facilitator structure IFS, or a component thereof. For instance, in one embodiment the analyzer grating G1 (that is, the grating arranged between object and detector) is moved ("scanned") laterally relative to an optical axis of the X-ray beam. Alternatively, phase stepping can also be achieved by moving the patient OB as in FIG. 1, or by moving the X-ray source, etc. This phase stepping motion causes a change of the fringe pattern which in turn can be recorded in the corresponding series for each step of the motion. This series of measurements form, for each geometrical ray, an associated phase curve. The phase curves are in general of sinusoidal shape and it has been found that each encodes the quantities of interest, in particular the dark-field signal, along with attenuation and phase change.

In more detail, the phase curves for each pixel/geometrical ray can be respectively analyzed, for instance by fitting to a sinusoidal signal model as described in Pfeiffer et al *Hard-X-ray dark-field imaging using a grating interferometer*, published in Nature Materials 7, pp 134-137 (2008), to effect the image generation. Preferably, there are at least three fitting parameters included in the three-channel sinusoidal model. The three fitting parameters represent, respectively, the three contributions phase-contrast, dark-field signal and attenuation. The sinusoidal model is fitted by image generator IGEN to the phase curves to so compute in particular the DAX- and/or Φ-image, and a attenuation (also called "transmission") image, although this is of lesser interest herein. Computation of the apparently superfluous transmission image may be required to correctly account for the three contrast effects as otherwise incorrect contributions are incurred in the DAX and/or Φ-channel.

An optimization procedure is used to fit the measured series of projections to the model. The procedure can be understood in terms of as cost function and the fitting operation can be formulated as an optimization problem. Any suitable optimization scheme such as gradient descent, conjugate gradients, Newton-Raphson, stochastic gradients, Maximum Likelihood approach, other statistical techniques or others are also envisaged. Non analytical methods such as neural networks or other Machine Learning techniques may also be used.

In general, an optimization problem for a signal model M has the following structure:

$$\mathrm{argmin}_{T,D,\varphi} F = \|\pi - S^{T,D,\varphi}(X)\| \quad (1)$$

wherein $S^{T,D,\varphi}(\bullet)$ is an at least three-channel modulator function that describes how the three contrast mechanism combine to modulate and transform the incoming (undisturbed) radiation X into the measured data π, and $\|\bullet\|$ a suitable similarity measure, a p-norm for instance, (squared) Euclidean distance, etc. Function F, the objective function (in this case a cost function) measures how well the signal model S "explains" (or "fits") the measured data π and the optimization task is how best to choose the parameters (T, D, φ) of the model, with the similarity measure $\|\bullet\|$ quantifying the goodness of fit, in case the cost or error. The task in the optimization is to improve the cost function by adjusting parameters (T, D, φ). In this case, the parameters are to be adjusted in the optimization so that the values ("cost") returned by the cost function F decreases. More than three channels may be used in signal model M, depending on the number of contrast mechanism one wishes to account for. In (1), F may be a function of residues (terms). Each residue quantifies a respective deviation, or cost, of given projection image from its prediction under model S.

More specially, in one embodiment, as a special case of (1), the following analytical signal model $F=\Delta^2$ optimization is used per pixel or geometrical ray:

$$\Delta^2(T,D,\varphi) = \Sigma_i w_i (M_i - I_i T(1 + V_i D \cos(\varphi - \alpha_i)))^2 \quad (2)$$

wherein $M_i$ are the measured data (taken from π), the undisturbed radiation "X" is represented by $I_i$, $V_i$, and $\alpha_i$ the blank scan intensities, visibilities, and phases, respectively. T, D, and φ are the three contrast modulators of S( ) above namely: transmission, dark-field, and differential phase for this image point. $w_i$ are optional statistical weights, usually selected to be equal or proportional to the inverse variance of the measured data $M_i$, and i indicates the phase steps. Following on from ( ), the task in (2) is to minimize the cost T $\Delta_2$ over the measured data M to find in particular the images D and ??. The right hand side of (2) may be understood as a sum of the residues.

The above described types of image generation algorithms (1), (2) are sometimes referred to as "phase retrieval" but this is for present purposes a misnomer as there is also the dark-field image co-generated in the fitting operation and so is in fact the transmission image as mentioned above. Other, Fourier based methods, such the one by Pfeiffer et al (cited above), and related ones, are also envisaged herein as phase retrieval algorithms in embodiments.

The abovementioned phase stepping operation requires time and this may lead to unfavorable results when imaging moving objects such as animal or human patients. More specifically, in the phase stepping of DAX- and Φ-imaging, a certain number of frames is required for image generation, and each frame acquisition takes time for exposure, data readout, and movement of the grating to the next position. The acquisition of these frames consumes a time interval of about one second. This is in the same order of magnitude as the duration of a heartbeat, so intensity fluctuations due to the heart motion interfere with the modulated fringe pattern of the DAX/Φ phase retrieval algorithms and this may lead to artifacts. These effects can be observed in a slot scan system as in FIG. 1, but is expected to also occur in a full FoV system.

A particular problem that arises from the longer acquisition time is in particular the relevance of cardiac motion as this causes motion artifacts to be recorded. One of the main reasons for the manifestation of the artifacts is that the patient OB does not comply with model assumptions (1), (2) on which the image generation is based. In (1), (2) a stationary imaged object is assumed. In particular, in (1), (2) it is assumed in the signal model that the transmission T is the same for all measurements $\pi$. In the presence of motion, however, the transmission T is not the same for all measurements $\pi$, but there are intensity changes being recorded, that are in addition to those intensity changes that are expected due to the phase stepping measurements. Unfortunately, if unaccounted for, these additional intensity changes are now wrongly attributed to changes in the other two channels, dark-field signal D and differential phase ??.

The proposed motion corrector system MCS is configured to account for the patient motion and thereby reduces motion artifacts in DAX or Φ-imaging. In order to remove, or at least reduce, motion artifacts caused by motion of the patient OB, in particular breathing or cardiac motion, the proposed motion corrector system MCS is broadly configured to apply adaptively cardiac and/or respiratory gating in the phase retrieval step. Specifically, and as will described more fully below, a two-step approach is proposed. Since motion creates data which are inconsistent with the model, the cost function after optimization is typically much larger than what is statistically expected. It has been observed that image location affected by motion artifacts in general return larger values of the cost function.

However, Applicant has found that a gating operation (i.e., discarding or down-weighting of parts of the data) as such is a double edged sword that cannot always trade-off successfully between two opposing objectives, namely low image artifacts and low image noise. Also, there is limited freedom to gate the acquisition since it needs to be ensured at the same time to acquire sufficient data for image generation, in particular the phase retrieval that relies on a number of steps i to have a well define stepping curve.

In more detail, Applicants have found that motion artifact reduction by simple gating does not necessarily reduce motion artifacts uniformly in the whole image. The motion artifact reduction is rather local and different for different image regions. Whilst motion artifacts are largely reduced in most locations, the amount of artifact reduction appears to depend upon the location in the image. This may be in particular the case if cardiac motion creates artifacts in one location but breathing motion creates artifacts in another location. What is more, there are even image regions where the artifact level is increasing, for instance because the phase stepping curve is poorly sampled due to the gating. In addition, it has been observed that a decreased level of artifact corruption comes at the expense of increased noise since fewer data points were used in the phase retrieval in some gating window schemes. To address both objectives, that is noise reduction and motion artifact reduction in the whole or in most regions of the image, the proposed motion correction system MCS is configured to proceed in two phases. Components of the proposed motion corrector MCS reference will now be explained in detail with reference to the block diagram of FIG. 2.

Figure 2:
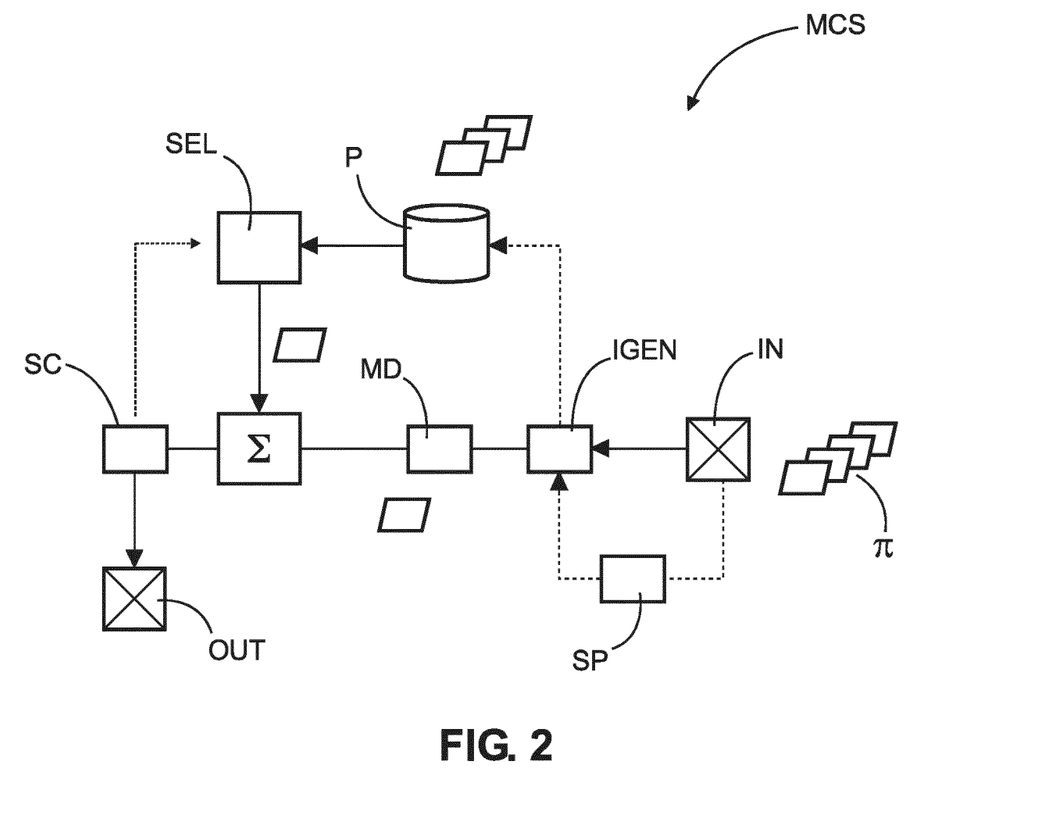
FIG. 2 is a diagram of a motion artifact correction system.

Broadly, input projection imagery $\pi$ is received at an input interface IN. The input imagery is processed in a manner to be described more fully below to produce motion artifact corrected dark-field and/or phase-contrast imagery which is output at output port OUT.

In one phase, a phase retrieval operation is performed based on the series of projection imagery $\pi$ obtained during the described phase stepping operation. It is this series of projection imagery $\pi$ that is then processed. Specifically, the image generator IGEN implements a phase retrieval algorithm to produce a first image such as a phase-contrast and/or dark-field image. This image will be referred to herein as the "main image".

In a further phase (which may occur before or after the above, earlier mentioned phase), a retrospectively gated phase retrieval is then performed in embodiments by the image generator IGEN in a previous preparatory phase or on demand during the operation of the motion correction system MCS.

This gated phase retrieval operation includes sampling, by a sampler SP, from the original set of projection images $\pi$, respective different sub-sets. Based on these subsets the image generator IGEN performs a respective phase retrieval operation on those different sub-sets only. In (2) above, the summation over i will hence run only over a subset of those indices associated with the sampled projection images. These operations result in different gated phase-contrast and/or dark-field images, referred to herein as "auxiliary" or "gated images". Each sample sub-set hence results in a respective gated image. These gated images may be stored in memory storage P.

For instance, one simple under-sampling scheme may include forming different subsets by choosing different samples of a certain fraction p, such as p=50%, of the all the available measured data $\pi$. Other fractional values of p are also envisaged. However, the fraction p needs to be balanced against the expected rise in noise contributions if p is too small. The fraction p may be adjustable by a user or the system adjusts this adaptively, for instance based on an entropy evaluator that examines the main image or the set of projection images. If the global image information is complex, higher values of p may be called for, otherwise p can be lowered. Alternatively, as will be explained further below p may be varied during the processing as a function of image location. The sampling may be randomized or may be guided by other considerations such as reasonable coverage of a full 360° phase of the remaining samples so that a proper phase retrieval is still possible. Reasonable may mean for instance that the largest gap between the phase samples is less than 90°.

A motion detector MD then examines the main image to localize one or more image regions which are, or may be, compromised by motion artifacts and flags up those one or more locations accordingly, with the respective flag indicating motion corruption, for example: "yes"=1 or "no"=0. This binary 0/1 flagging is an instance of "hard" flagging. A "soft", or continuous flagging, might also be implemented, for example by providing a "likelihood" of artifacts being present, the said likelihood ranging from 0 to 1 for example.

In embodiments, the motion detector MD may be implemented by thresholding the cost function used in the phase retrieval algorithm. For instance, in embodiments the function $F=\Delta^2$ in eq (1) is used, or any other. Other motion detection criteria may also be used. Specifically, if the cost function is properly set up as a noise weighted least squares cost function, its values are expected to follow the ??$^2$ distribution. The likelihood function that indicates the likelihood can be the cumulative probability derived from this distribution. Alternatively, in a discrete version, all image points where the cost function is more than 2 standard deviations away from the expectation value of the ??² distribution can be flagged as "yes"=1.

A selector SEL selects from storage P, for some or each image pixel that has been found by the motion detector MD to be compromised by motion artifacts, a respective gated image. In embodiments the selector SEL selects for a given motion artifact corrupted pixel or patch, the gated image that has the smallest cost function F at the respective pixel as identified by the motion detector in the main image. Alternatively, or in addition, the selector SEL selects the gated image that has locally (that is, in the patch) the smallest standard deviation, for instance, the one that has the least level of artifact corruption, or other. In general, an agreed measure function or score is used to measure the goodness of the selected gated image per patch or pixel in the main image.

The goodness or "best" gated image is measured according to a score threshold. There may be more than one "best" gating image, in which case a random operation may be performed to pinpoint a single one, or an average of the best gating images can be used.

The selection operation thus determines the best gating window or the best gated image that is best suited for reducing/eliminating the motion artifacts found by the motion detector in the main image. The selection operation proceeds pixel-wisely or region("patch")-wisely and returns for each different pixel/region in the main image, in general a different gated image. In other words, the selection operation by the selector establishes a mapping where to each region or pixel in the main image there is associated a respective gated image from storage P that is best suited to eliminate or reduce the motion artifact at the respective location in the main image.

This selector mapping may be adaptive in that the fraction p is adapted based on evaluation of local information in the main image. Based on this evaluation, p is determined and based on this value, the pool is then build up by sampler SP from which the selector then selects the right gated image. In other words, in certain embodiments the pool does not always contain the same gated images for a given main image (although this is indeed the case in some embodiments) but the pool content varies from image location to image location in the main image. The evaluation may be done by the mentioned entropy analyzer to establish image information complexity and the fraction p is then determined based on the entropy at the considered image location (pixel or patch).

A combiner Σ then combines image information from the main image with image information from the best gated image found by the selector SEL to so eliminate, or at least reduce, the image artifacts at the respective location. The combination operation by combiner Σ proceeds in general pixel-wisely or at least region-wisely.

From the above it will be understood that all those pixels or regions in the main image that are were not found to be compromised by motion artifacts are maintained and are not changed. However, those image pixels (x,y) that have been found by the motion detector to be motion compromised will be changed based on the associated gated image.

The combination operation by combiner Σ may proceed by simply replacing the motion corrupted pixel at (x,y) in the main image by image information at the respective location (x,y) in the associated (and hence "best") gated image. Optionally, a linear combination of the two pixel values, that is, from the main image and the associated gated image, can be performed. In this linear combination, the weights for each pixel/patch may depend on a quality measure, for instance the value of the cost function at that pixel/patch.

More specifically, the weights are "sliding" with high weight given to either the original value or the pixel in the gated image depending on the extent to which there is motion corruption. For instance, if high motion corruption is found at the respective location in the main image, more weight is given to the image value derived from the associated gated image. However, if there is less motion corruption found at the respective image location, the weight is reduced in favor of a weight increase for the image value in the main image. In other words, the weights are in proportion to the level of motion corruption found by the motion detector MD at the given image location in the main image.

Once the combination operation by combiner Σ has been completed the so found combined image is then output at output port OUT as a motion artifact reduced image. This can then be stored, displayed on a display device or otherwise processed.

The above described embodiments of the motion corrector MCS may be understood as embodiments of "hard" gating. In other words, only the selected projection images as selected by the selector SEL are processed by the image generator IGEN when solving (1), (2) to generate the gated images.

In an alternative embodiments, a "soft" gating scheme is envisaged where punitive weights are applied by the image generator when solving (1), (2) to relatively down-weigh the residues for non-selected projection imagery to so give more weight to the residues of the selected imagery. In (2), the punitive weights are envisaged over and above the optional statistical weights $w_i$ in (2) for the individual phase steps i.

In yet other words, in soft gating more (in particular all) projection images π are considered in the optimization of (1), (2). However, residue terms that relate to non-selected projection imagery are (at least) relatively down-weigh compared to residue terms that relate to selected projection imagery. Relative down-weighing includes either applying a higher weight to the reside for selected projection images and/or or applying lower weights to the residue for unselected projection images. In sum, in soft gating, excluded (non-selected) projection images are still considered for the phase retrieval (1), (2) but their contributions to the objection function F is lessened. The modes of operation of the image generator based on the above described soft or hard gating scheme may hence be referred to herein collectively as a gated application of the image generation algorithm, compared to the (ungated) image generation of the main image where more (in particular all) projection images where considered equally in the optimization (1), (2).

Optionally, the system MCS may also include a sanity checker SC. This is because it has been found that the sampling operation or the selection operation by selector SEL may sometimes introduce undesirable aliasing effects which may result in true image structures being removed in the combined image. The aliasing effects may cause real structures in the main image to be eliminated due to the selection of the sub-sets themselves by selector SEL or sampler SP. The sanity check is performed only for image location where there could be a dispute, namely for image locations flagged up by the motion detector MD.

The sanity checker SC interacts with the combiner Σ. The sanity checker SC itself performs a selection operation from the measured data set π but this selection is based on sub-sets that are the set complements of those sets selected by the selector. This complementary selection is performed separately for each flagged image location in the main image and the following is understood to apply per each (or some) such flagged image location in the main image.

In more detail and as explained above, each gated image selected by the selector for combination has been obtained by a certain sub-selection of projection images. The sanity checker than considers for this selection the sub-set of projection images not selected, that is, the (set) complement. From this sub-set of complementary projection images a corresponding series of transmission images is computed. This can be done for instance by using Fourier-based methods where the diffraction pattern imprinted by the image facilitator structure IFS (such as the interferometer (G1, G2)) is eliminated from the projection imagery $\pi$ in the complementary sub-set. Alternatively, one subtracts the fringe pattern from the images of the stepping curve based on the calculated phase-contrast image (phase of the fringe pattern) and dark-field image (amplitude of the fringe pattern).

Pair-wise difference images are then formed by between each of the transmission images and the proposed combined image obtained by the combiner. The pair-wise difference operation may result in certain peaks to be formed in the difference images. A track operation is then performed to track those peaks. If a peak is found to propagate through the series of difference images, this is then taken to indicate that the respective image value in the combined image at the considered location is spurious and in this case the original image value from main image is then retained at the considered flagged image location. In other words, the replaced value as returned by the combiner if the proposed combined image is rejected.

If, however, no such propagation is found this is an indication that the image value produced by the combiner is realistic and represents genuine image structure and the proposed image value in the combined image is allowed to remain. In other words, the sanity checker based on the propagation evaluation, either rejects or retains the image values in the combined image and, if rejected, maintains the original image information from the main image.

In addition or instead, a conspicuous indicator value is included at the respective image location to indicate to the viewer that this location cannot be trusted as this may or may not be marred by motion artifacts. The conspicuous indicator value may be chosen as one that markedly differs from values in its neighborhood, such as "1" or "0" in case of grey value rendering palette as commonly used on radiography.

Figure 3:
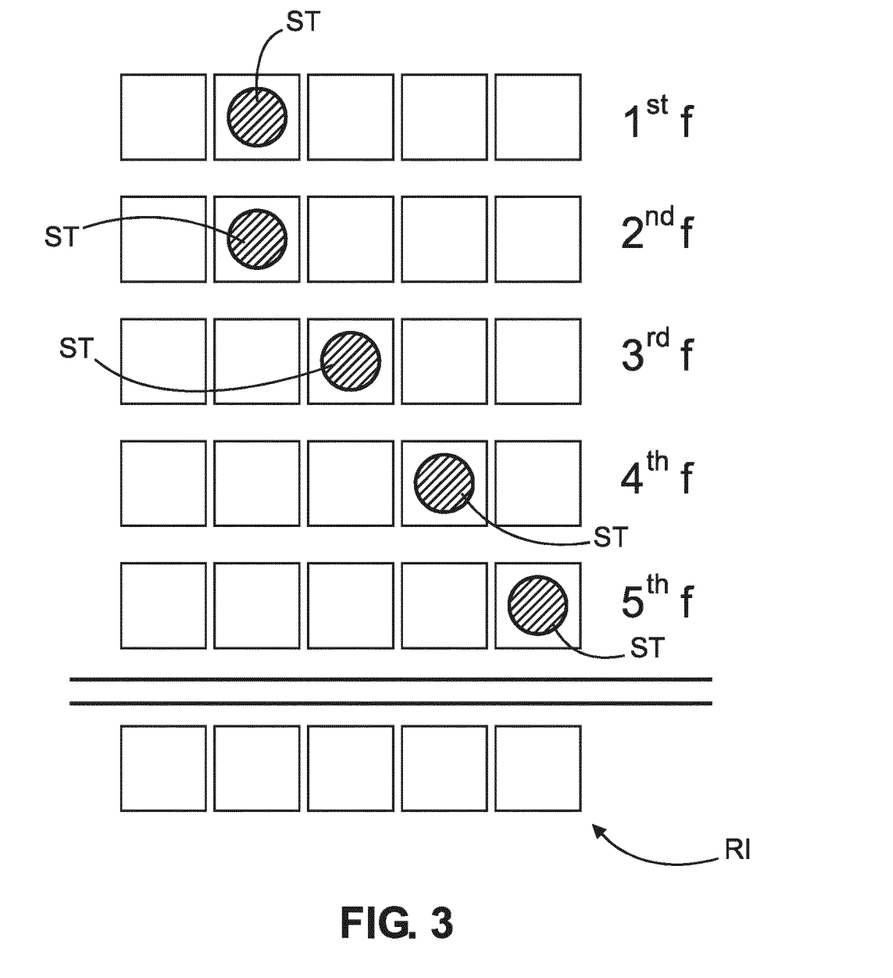
FIG. 3 is an illustration of an effect of a combination step where image information is combined.

FIG. 3 is a diagrammatic illustration as to how this aliasing effect may come about. Assuming in a toy example, that the field of view consists of five pixels as shown in FIG. 3, and the stepping curve obtained in the phase stepping operation consists of 5 frames $1^{st}$ f-$5^{th}$ f from top to bottom as shown diagrammatically in FIG. 3. During the first and second frame there is a small object ST, captured in the second pixel from the left. During the last three frames, the object ST moves in a linear non-periodic motion one pixel to the right. If the processing is performed using local (for each pixel separately) minimization of the residuum of the cost function with a sampling as in the system of FIG. 2 (or method of FIG. 5 below), it can be seen that the resulting image RI will consist of 5 blank pixels.

This "aliasing" effect can be undesirable if one considers the object ST to be a small structure that may be relevant for diagnostic imaging. In particular, the local minimization of the cost function residuum, can be problematic for diagnostic accuracy if a linear motion is captured in the imagery.

The sanity checker SC implements an approach where the similarity of the received projection imagery is analyzed based on transmission information. In this way it can be established if genuine absorbing features ST are present in the phase stepping sequence, and if there is linear motion (propagation), for which frame the motion starts and for which pixel. The above described embodiment of the sanity checker SC acts as a post-processor relative to the output of the combiner $\Sigma$.

Alternatively, the sanity checker SC may be used as a pre-processor, upstream the combiner $\Sigma$. In this embodiment, the transmission information can be used to constrain the sampler SP operation in forming the sub-sets of projection images from which DAX/$\Phi$-imagery is the generatable for use by the combiner $\Sigma$. In particular, in the example in FIG. 3, for the second pixel from the left, only the first two frames $1^{st}$ f,$2^{nd}$ f would be allowed to be considered for motion artifact reduction at all. This embodiment will be explained in more detail below.

Whilst the proposed system MCS has been found to yield satisfactory results when it comes to oscillatory or periodic motion, the system MCS may fail and produce wrongful imagery in case there is non-period or non-oscillatory motion present in the imaged object OB. In particular, in the latter case the use of the sanity checker is SC proposed whilst the sanity checker SC may not be required if the system MCS is used in scenarios where only period motion that can occur such as cardiac motion or respiratory motion. The sanity checker SC may be switched off and on by the user.

Operation of the sanity checker SC in particular as a pre-processor is now explained in more detail, including further embodiments.

The sanity checker SC operation relies on obtaining a transmission image for some or each of the projection images from the stepping curve. This can be either achieved through a Fourier decomposition, as described by e.g. Han Wen et al Wen in "*Fourier X-ray scattering radiography yields bone structural information*", Radiology 251.3 (2009), pp 910-918 or other, such as for example, subtraction of the modulation overlaying the image based on the phase-contrast (phase of the modulation) and dark field (amplitude of the modulation) as calculated by the combiner. A third possibility would be to use all sub-sets of consecutive projection images $\pi$ (e.g. if $\pi$ contains 10 images, use images with frame nos. 1, 2, 3) to calculate transmission images.

In case a method similar to the one described by Han Wen et al. is used it may be favorable to introduce a relatively high frequency Moiré fringe pattern onto the detector. Thus, a transmission image should be calculated from each of the images of the stepping curve.

There are also other embodiments envisaged where the sanity checker does not act as a post-processor, that is on the combined image, but acts in a pre-phase as a filter to ensure that only certain projections sub-sets are allowed to be processed into the gated images and are admitted into the pool. In some of such pre-phase embodiments of the checker SC, the transmission images may be compared to each other—e.g. through subtraction of the images one from the other, and, based on a certain threshold, it is determined if and where motion is present. Then, those frame numbers in $\pi$ are determined that are not impacted by motion. In addition, a comparison of the neighboring pixel for some or all the image series $\pi$ will reveal the additional information on whether the motion is linear or oscillating.

The pre-selection of the images of the image series $\pi$ that are allowed to be processed into gated images for selection by selector SEL may be performed based on the following logic of the sanity checker: If absorption levels change significantly between frames, i.e. if an absorbing feature SF is present in one or several of the frames in a pixel and then disappears or appears in a different pixel, then the images from the stepping curve that depict this feature should be chosen. In other words, what is proposed herein in embodiments is to allow only those frames to be processed into gated images (and then admitted into the pool) that represent the absorbing structure and not merely minimize the cost function locally, as this does not necessarily guarantee that the feature will be preserved in the resulting image RI.

The definition of "absorbing feature" will differ from case to case, and it is suggested in embodiments to use a thresholding against neighboring pixels. In more detail, and in one embodiment, if a deviation of the absorption relative to the neighboring pixels exceeds a certain threshold th, eg by th=10%, then this may be taken to indicate that an absorbing feature ST is present at the considered pixel location.

If the above filtering for suitable frames that do not record linear movement results in an insufficient number (e.g. 1 or 2) of remaining images for "normal" processing flow in the MSC, it is proposed to directly use the signals of a single transmission image from π derived from subtraction of the overlaying fringe modulation, and to place a marker at the respective location in the main image (dark-field or phase contrast) to clearly indicate to the user that there is motion artifacts present The marker may be set by replacing for example the image value by unrealistic values such as "1" or "0" in case a grey value palette is used.

Figure 4:
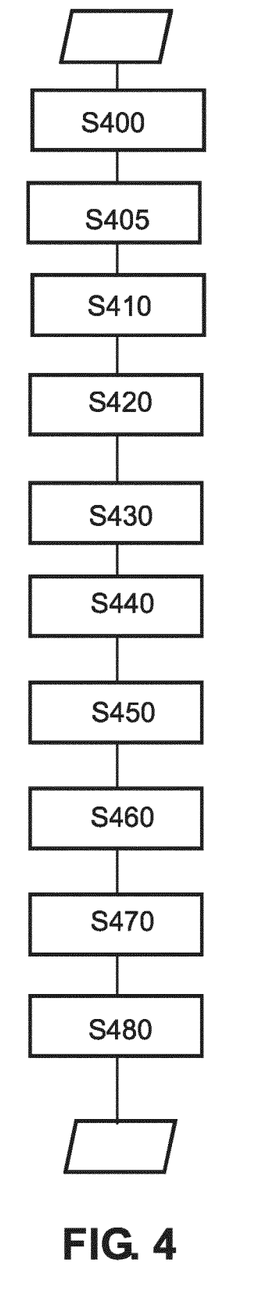
FIG. 4 is a flow chart of a method for image processing.

Referring now to FIG. 4, this shows a flow chart of a proposed image processing method that may underlie operation of motion corrector MCS of FIG. 2. It will be understood however that the method steps described in the following constitute a teaching in their own right and are not necessarily tied to the specific architecture shown in FIG. 1 or 2.

Broadly the proposed new image processing method for motion artifact correction in particular for DAX or Φ images includes a step S410 where projection data π is received as input data. The input data is presumably motion corrupted. Retrospective gating is used to form gated images and some of these may then be used to "repair" local manifestations of motion corruption in a computed DAX or Φ image.

More specifically, the input data received at step S410 includes a series of projection images for a given projection direction. It is mainly radiography that is envisaged herein. The series of projection images was acquired by an X-ray imaging apparatus of an object PAT at a given projection direction. The X-ray imaging apparatus is understood to be configured for phase and/or dark-field imaging. In embodiments this includes having an image facilitator structure IFS arranged between the X-ray source and the detector D of the imaging apparatus. The image facilitating structure IFS, such as a grating(s), interacts with the radiation that passes therethrough and through the patient, and modulates the radiation into an intensity pattern that can be analyzed by an image processing operation. The image processing operation may include a phase retrieval operation to extract in particular the phase-contrast and/or the dark-field image signal.

In step S420 the phase retrieval operation is so applied to compute a first image, referred to herein as the main image, from the series of projection images for a given projection direction. For this operation preferably the whole of series of the projection imagery is used. The phase retrieval operation may be based on improving an objective function. In embodiments the objective function is a cost function and the phase retrieval involves computations to minimize the cost function. Minimizing may include adjusting fitting variables, so as to make the cost function return reduced values. Alternatively, phase retrieval may also be formulated in terms of maximizing a utility function.

The so obtained main image is a phase-contrast or dark-field image which however is expected to be compromised by motion artifacts due to motion corruption in the projection imagery as the patient may have moved during projection image acquisition. The projection imagery may include motion artifacts caused or imparted by cardiac activity or breathing activity or other. The motion may be periodic or non-period.

In step S430 a motion artifact is detected in the first image based on a motion detection algorithm. The motion artifact detection S430 proceeds preferably locally, that is per image location. In following "image location" is meant to either indicate a pixel location or a patch, a neighborhood or region, around such as pixel.

As mentioned above, in embodiments the phase retrieval algorithm in step S420 is based on an optimization of the objective function, and it is the values of the objective function for a given image location such as a pixel or voxel that is thresholded to decide whether or not there is image motion.

Alternatively, the motion detection algorithm analyses in-image information or considers a short sequence of projection images for the respective image location to establish motion corruption.

In step S450, if a motion artifact has been detected in step S430, then, for the considered image location, a part of the first image is combined with a part of an auxiliary image to obtain a combined image.

The auxiliary image has been previously pre-computed by applying the image generation algorithm to a sub-set of the series of projection images π received at step S410.

In more details and in embodiments, there is a gating operation in form of a selection step S440 in which a selection operation is performed. In the selection operation S440, the auxiliary image is selected for the considered image location from a pool of auxiliary images. The selection S440 is based on a score or measure. The score may represent the amount of motion corruption there is at an image location (in the auxiliary image) that corresponds to the considered location in the main image. Standard-deviation in the image location (taken as a patch) is a score according to one embodiments and the auxiliary image having the least standard deviation or a standard deviation less than a threshold at the corresponding image location is selected S440. In other embodiments the cost function value itself is used as a score and the auxiliary image that returns the least cost or at least a cost less than a threshold is selected S440. Other embodiments of the selection score are also envisaged. The auxiliary images in the pool are preferably pre-computed from different such sub-sets sampled in a sampling step S425 from some or all original projection images 71 The auxiliary or gated images are computed by the phase retrieval algorithm, preferably the one used in step S420, but this time restricted to each of the sub-sets of projection images. Again, rather than selecting some sub-set of projection images at the exclusion of others, it is also possible to admit all projections but to then at least relatively down-weigh the others (the not selected ones) in respect of their contribution to the cost function as mentioned above at FIG. 2 in relation to "hard" and "soft" gating. Alternatively, a different phase retrieval algorithm is used to obtain the gates images. The computing of the gated images may be performed by the same computing entity (machine or module) as used for step S420 when computing the main image. Alternatively, a different entity may be used running the same or a different phase retrieval algorithm. The pool of gated images may have been computed elsewhere and stored in a storage P and are accessed later by the selectin step S440.

The pool of auxiliary images may be sampled S425 and computed S430 on demand or may be pre-computed and kept in storage to be used for other image locations for the same main image. The auxiliary images can be computed before step S420 or thereafter. The pool of gated images may remain constant throughput a part or the whole operation for a given main image, so the selection happens from the same pool. Alternatively, the composition of the pool changes during execution of the method, due to an adaptive sampling step that resamples in dependence for example on the given image location of the main image currently processed.

In step S460, the main image and the auxiliary image are combined. The combination is local and is performed preferably only for those image locations of the main image where, in step S430, motion corruption was found. Combination may include replacing an image value(s) at the location with image value(s) at the corresponding location in the associated auxiliary (gated) images. Alternatively, a linear or non-linear combination is formed and this is used for replacing the value in the main image at the considered image location.

The proposed method may further include an optional step S470 where a sanity check is performed.

The sanity checking may include computing based on a different sub-set of projection imageries a corresponding series or transmission images. The sanity check may be performed for some or each of those image location(s) of the main image where in step S430 motion corruption was found.

The sanity checker step S470 includes forming pairwise difference images between the series of transmission images and the combined image as obtained at step S460. The series of difference images so obtained is then analyzed to find whether certain difference values, or peak values, propagate through the series of difference images. Image structure tracking schemes can be used for this. If such propagation can be established, the image value at the considered image location in the combined image is replaced by the original value at the respective image location in the original first image. In other words, the proposed image value in the combination step is rejected. If, however, no such propagation can be established the image value at the considered image location as computed in the combining step is affirmed and maintained.

The sanity checking operation at step S470 allows avoiding that a true image structure is eliminated by aliasing effect caused by the selection or sampling operation which underlie the respective auxiliary image that has been used in the combination step. The sanity check step is preferably used when there is non-periodic motion or non-oscillatory motion expected to have occurred during acquisition of the original measurement data $\pi$. At a follow-up step the combined image, possibly sanity checked, is then output at the next step as a motion artifact reduced image.

Instead of applying the sanity check step S470 as a post-processing step after the combiner step S460, it also envisaged herein to instead apply pre-processing sanity check step upstream the combiner step S460. In this embodiment, the projection images are converted in step S400 into transmission imagery be elimination of the fringe pattern, for instance by Fourier methods and subtraction. A motion analysis, eg tracking, is performed. Frames that represent at one or more image locations linear motion are excluded at step S405 to so reduce the set of original projection images. It this reduced set of projection images $\pi'$ that is then processed from step S430 onwards as described above.

At step S480 the combined image, optionally sanity checked, is output for storage, visualization, or any other processing.

The components of the image processing system IPS, in particular the MSC, may be implemented as software modules or routines in a single software suit and run on a general purpose computing unit PU such as a workstation associated with the imager IM or a server computer associated with a group of imagers. Alternatively, the components of the image processing system IPS may be arranged in a distributed architecture and connected in a suitable communication network.

Some or all components may be arranged in hardware such as a suitably programmed FPGA (field-programmable-gate-array) or as hardwired IC chip.

One or more features disclosed herein may be configured or implemented as/with circuitry encoded within a computer-readable medium, and/or combinations thereof. Circuitry may include discrete and/or integrated circuitry, application specific integrated circuitry (ASIC), a system-on-a-chip (SOC), and combinations thereof, a machine, a computer system, a processor and memory, a computer program.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for image processing, comprising:
   an imaging apparatus configured to acquire a series of projection images of an object, the imaging apparatus configured for at least one of phase-contrast and dark-field imaging;
   an input interface for receiving the series of projection images acquired by the imaging apparatus for a given projection direction;
   an image generator configured to apply an image generation algorithm to compute a first image based on the series of projection images;
   a motion artifact detector configured to detect a motion artifact in the first image;
   a combiner configured to combine, if a motion artifact is so detected at an artifact location in the first image, the first image with at least one auxiliary image at a location corresponding with the artifact location in the first image to obtain a combined image at the artifact location, the auxiliary image previously computed by a gated application of the image generation algorithm in respect of a subset of the series of the projection images; and
   an output interface to output the combined image.

2. The system of claim 1, further comprising a selector configured to select the auxiliary image from a pool of such auxiliary images computed based on different subsets.

3. The system of claim 2, wherein the image generation algorithm is based on an objective function.

4. The system of claim 3, wherein the selection is based on a score.

5. The system of claim 4, wherein the score includes a value returned by the objective function.

6. The system of claim 3, wherein the motion detector is configured to detect the motion artifact based on a value of the objective function for the first image.

7. The system of claim 1, comprising a sanity checker, configured to compute, based on a second subset, a series of transmission images and pairwise differences with the combined image, and to retain, at an image location in the combined image, image information from the first image, if the difference values are found to propagate through the series of transmission images.

8. The system of claim 1, wherein the series of projection images as received at the input interface are provided by a sanity checker as a sub-set from an original set of projection images, the sanity checker previously computing, from the original set of projection images, transmission images, and the sanity checker SC configured to exclude, based on the transmission images, one or more images from the original set of projection images, wherein the excluded one or more projection mages represent linear motion at at least one image location.

9. A method of image processing, comprising:
   receiving a series of projection images acquired by an imaging apparatus of an object for a given projection direction, the imaging apparatus configured for at least one of phase-contrast and dark-field imaging;
   applying an image generation algorithm to compute a first image based on the series the projection images;
   detecting a motion artifact in the first image;
   combining, if a motion artifact is so detected at an artifact location in the first image, the first image with at least one auxiliary image at a location corresponding with the artifact location in the first image to obtain a combined image at the artifact location, the auxiliary image previously computed by a gated application of the image generation algorithm in respect of a subset of the series of the projection images; and
   outputting the combined image.

10. The method of claim 9, further comprising:
    computing, based on a second subset, a series of transmission images and pairwise differences with the combined image, and retaining, at an image location in the combined image, image information from the first image, if the difference values are found to propagate through the series of transmission images;
    wherein the series of projection images are provided as a sub-set from an original set of projection images obtained by:
    computing, from the original set of projection images, transmission images, and excluding, based on the transmission images, one or more images from the original set of projection images, wherein the excluded one or more projection mages represent linear motion at least one image location.

11. A non-transitory computer-readable medium for storing executable instructions, which cause a method to be performed for image processing, the method comprising:
    receiving a series of projection images acquired by an imaging apparatus of an object for a given projection direction, the imaging apparatus configured for at least one of phase-contrast and dark-field imaging;

applying an image generation algorithm to compute a first image based on the series the projection images;
detecting a motion artifact in the first image;
combining, if a motion artifact is so detected at an artifact location in the first image, the first image with at least one auxiliary image at a location corresponding with the artifact location in the first image to obtain a combined image at the artifact location, the auxiliary image previously computed by a gated application of the image generation algorithm in respect of a subset of the series of the projection images; and
outputting the combined image.

\* \* \* \* \*